(12) United States Patent
Crozier et al.

(10) Patent No.: US 9,977,100 B2
(45) Date of Patent: May 22, 2018

(54) COIL ARRANGEMENT FOR USE IN A MAGNETIC RESONANCE IMAGING SYSTEM

(75) Inventors: Stuart Crozier, Wilston (AU); Adnan Trakic, Talgum (AU); Ewald Weber, Alexandra Hill (AU); Bing Keong Li, Springfield Lakes (AU); Hua Wang, St. Lucia (AU)

(73) Assignee: The University of Queensland, St. Lucia, Queensland (AU)

( * ) Notice: Subject to any disclaimer, the term of this patent is extended or adjusted under 35 U.S.C. 154(b) by 769 days.

(21) Appl. No.: 13/262,145

(22) PCT Filed: Mar. 30, 2010

(86) PCT No.: PCT/AU2010/000365
§ 371 (c)(1),
(2), (4) Date: Nov. 23, 2011

(87) PCT Pub. No.: WO2010/111736
PCT Pub. Date: Oct. 7, 2010

(65) Prior Publication Data
US 2012/0068709 A1 Mar. 22, 2012

(30) Foreign Application Priority Data
Mar. 31, 2009 (AU) ................ 2009901386

(51) Int. Cl.
*G01R 33/3415* (2006.01)
*A61B 5/055* (2006.01)
(Continued)

(52) U.S. Cl.
CPC .......... *G01R 33/3415* (2013.01); *A61B 5/055* (2013.01); *G01R 33/365* (2013.01); *A61B 5/4528* (2013.01); *A61B 5/4533* (2013.01)

(58) Field of Classification Search
CPC .. G01R 33/365; G01R 33/3415; A61B 5/055; A61B 5/4528; A61B 5/4533
See application file for complete search history.

(56) References Cited

U.S. PATENT DOCUMENTS 4,766,383 A * 8/1988 Fox et al. .................. 324/318
4,825,162 A 4/1989 Roemer et al.
(Continued)

FOREIGN PATENT DOCUMENTS

| DE | 198 44 762 A1 | 4/2000 |
|----|---------------|--------|
| WO | 2006/094354 A1 | 9/2006 |
| WO | 2008/116263 A1 | 10/2008 |

OTHER PUBLICATIONS

Hon Tat Hui; "Decoupling methods for the mutual coupling effect in antenna arrays: a review"; Recent patents on Engineering 2007, vol. 1, No. 2, pp. 187-193.*
(Continued)

*Primary Examiner* — Dixomara Vargas
(74) *Attorney, Agent, or Firm* — Nixon & Vanderhye P.C.

(57) ABSTRACT

A coil arrangement for use in a magnetic resonance imaging system, the imaging system being for generating a magnetic imaging field in an imaging region, the coil arrangement including at least three coils for at least one of transmitting, receiving or transceiving an electromagnetic field, each coil being provided on a coil geometry and being substantially orthogonal.

24 Claims, 17 Drawing Sheets

(51) Int. Cl.
*G01R 33/36* (2006.01)
*A61B 5/00* (2006.01)

(56) References Cited

U.S. PATENT DOCUMENTS

| | | | | |
|---|---|---|---|---|
| 5,351,688 A * | 10/1994 | Jones | | 600/422 |
| 5,394,087 A * | 2/1995 | Molyneaux | | 324/318 |
| 5,430,378 A * | 7/1995 | Jones | | 324/318 |
| 5,500,596 A * | 3/1996 | Grist et al. | | 324/318 |
| 5,543,711 A * | 8/1996 | Srinivasan et al. | | 324/318 |
| 5,578,925 A * | 11/1996 | Molyneaux et al. | | 324/318 |
| 5,777,474 A * | 7/1998 | Srinivasan | | 324/318 |
| 5,905,378 A * | 5/1999 | Giaquinto et al. | | 324/318 |
| 5,929,639 A * | 7/1999 | Doty | | 324/318 |
| 6,084,411 A * | 7/2000 | Giaquinto et al. | | 324/318 |
| 6,317,091 B1 * | 11/2001 | Oppelt | | 343/742 |
| 6,493,572 B1 * | 12/2002 | Su et al. | | 600/422 |
| 6,504,369 B1 * | 1/2003 | Varjo et al. | | 324/318 |
| 6,516,213 B1 | 2/2003 | Nevo | | |
| 6,522,135 B2 * | 2/2003 | Miller | G01R 33/441 | 324/300 |
| 6,624,633 B1 * | 9/2003 | Zou et al. | | 324/318 |
| 6,680,610 B1 * | 1/2004 | Kyriakos et al. | | 324/307 |
| 6,771,070 B2 * | 8/2004 | Lee | | 324/318 |
| 6,781,371 B2 * | 8/2004 | Taherian et al. | | 324/303 |
| 6,836,118 B2 * | 12/2004 | Molyneaux et al. | | 324/319 |
| 6,876,201 B2 * | 4/2005 | Takizawa et al. | | 324/318 |
| 6,894,496 B2 * | 5/2005 | Molyneaux et al. | | 324/318 |
| 6,900,633 B2 * | 5/2005 | Sauer | G01R 33/441 | 324/307 |
| 6,900,635 B1 | 5/2005 | Petropoulos et al. | | |
| 6,930,481 B2 | 8/2005 | Okamoto et al. | | |
| 6,975,115 B1 * | 12/2005 | Fujita et al. | | 324/318 |
| 7,049,818 B2 * | 5/2006 | Rinneberg et al. | | 324/318 |
| 7,088,104 B2 * | 8/2006 | Bottomley | | 324/328 |
| 7,091,721 B2 | 8/2006 | Jevtic | | |
| 7,098,659 B2 * | 8/2006 | Reykowski et al. | | 324/309 |
| 7,233,147 B2 * | 6/2007 | Duensing | | 324/318 |
| 7,298,145 B2 * | 11/2007 | Neufeld et al. | | 324/318 |
| 7,333,849 B1 * | 2/2008 | Su et al. | | 600/422 |
| 7,348,778 B2 * | 3/2008 | Chu et al. | | 324/318 |
| 7,391,213 B2 * | 6/2008 | Watkins | G01R 33/34046 | 324/307 |
| 7,394,251 B2 * | 7/2008 | Lin | | 324/309 |
| 7,446,528 B2 * | 11/2008 | Doddrell et al. | | 324/318 |
| 7,449,888 B1 * | 11/2008 | Malik et al. | | 324/318 |
| 7,479,784 B2 * | 1/2009 | Lee | | 324/318 |
| 7,570,054 B1 * | 8/2009 | Lin | | 324/309 |
| 7,646,199 B2 * | 1/2010 | Dannels et al. | | 324/318 |
| 7,683,620 B2 * | 3/2010 | Lin | | 324/309 |
| 7,701,209 B1 * | 4/2010 | Green | | 324/307 |
| 7,764,065 B2 * | 7/2010 | Biber et al. | | 324/318 |
| 7,830,147 B2 * | 11/2010 | Okamoto et al. | | 324/318 |
| 7,877,129 B2 * | 1/2011 | Takahashi et al. | | 600/410 |
| 7,898,252 B2 * | 3/2011 | Crozier et al. | | 324/307 |
| 7,898,255 B2 * | 3/2011 | Ochi et al. | | 324/318 |
| 7,999,541 B2 * | 8/2011 | Chisholm | G01N 24/087 | 324/300 |
| 7,999,548 B1 * | 8/2011 | Brown et al. | | 324/318 |
| 8,041,410 B2 * | 10/2011 | Zeijlemaker | A61N 1/3718 | 600/16 |
| 8,055,326 B1 * | 11/2011 | Dworkin et al. | | 600/422 |
| 8,148,989 B2 * | 4/2012 | Kopp | G01V 3/08 | 324/318 |
| 8,179,136 B2 * | 5/2012 | Chan et al. | | 324/318 |
| 8,188,740 B2 * | 5/2012 | Ninomiya et al. | | 324/318 |
| 8,299,793 B2 * | 10/2012 | Riederer et al. | | 324/318 |
| 8,320,991 B2 * | 11/2012 | Jascob | A61B 90/36 | 600/420 |
| 8,332,036 B2 * | 12/2012 | Hastings | A61N 1/0587 | 607/32 |
| 8,471,558 B2 * | 6/2013 | Chisholm | G01N 24/087 | 324/300 |
| 8,581,588 B2 * | 11/2013 | Driesel et al. | | 324/322 |
| 8,692,553 B2 * | 4/2014 | Schmidig | | 324/322 |
| 8,831,703 B2 * | 9/2014 | van der Kouwe et al. | | 600/410 |
| 8,917,091 B2 * | 12/2014 | Le Prado | G01C 19/62 | 324/244 |
| 9,037,213 B2 * | 5/2015 | Roth | G01R 33/028 | 600/410 |
| 2004/0000908 A1 | 1/2004 | Molyneaux et al. | | |

OTHER PUBLICATIONS

International Preliminary Report on Patentability (IPRP) (Chapter I) for PCT/AU2010/000365, dated Oct. 4, 2011.
International Search Report for PCT/AU2010/000365, dated May 31, 2010.
Office Action issued in corresponding German Application No. 11 2010 001 412.4 dated Mar. 25, 2015 (with English language translation).
Katscher, Ulrich, et al., "Transmit Sense," Magnetic Resonance in Medicine, 2003, vol. 49, No. 1, pp. 144-150.
Li, Bing Keong, et al., "Focused, Eight-Element Transceive Phased Array Coil for Parallel Magnetic Resonance Imaging of the Chest-Theoretical Considerations," Magnetic Resonance in Medicine, 2005, vol. 53, No. 6, pp. 1251-1257.
Weber, Ewald, et al., "A Novel 8-Channel Transceive Volume-Array for a 9.4T Animal Scanner," Proc. Intl. Soc. Mag. Reson. Med., 2008, vol. 16, p. 151.

* cited by examiner

COIL ARRANGEMENT FOR USE IN A MAGNETIC RESONANCE IMAGING SYSTEM

This application is the U.S. national phase of International Application No. PCT/AU2010/000365, filed 30 Mar. 2010, which designated the U.S. and claims priority to Australia Application No. 200901386, filed 31 Mar. 2009, the entire contents of each of which are hereby incorporated by reference.

BACKGROUND OF THE INVENTION

The present invention relates to a coil arrangement for use in a magnetic resonance imaging system, a method for use in determining a coil arrangement for use in a magnetic resonance imaging system and in particular to a coil arrangement having mutually orthogonal coils.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

In MRI, when a substance such as the human tissue is exposed to a strong and uniform polarizing static magnetic field $B_0$, the spins of abundant water hydrogen protons in the tissue align their individual magnetic moments along the magnetic field $B_0$, in a parallel or anti-parallel energy state. There then exists a net magnetic moment of the spin ensemble that is directed along the polarizing flux (low energy or parallel state) and precesses at the characteristic Larmor frequency.

If a spatially homogeneous RF field, $B_1$, oscillating near the Larmor frequency is imposed on the imaged tissue perpendicular to the polarizing field $B_0$, the net longitudinal magnetization, $M_z$, may be 'tipped' or rotated into the plane (x-y) perpendicular to the magnetic field $B_0$ to generate a net transverse magnetization (or the excited state). When the RF field $B_1$ is expired, the net magnetization relaxes back to its original low energy state that existed before the RF field $B_1$ was applied by emitting energy in the form of an RF-signal, or colloquially free induction decay (FID), that may be captured and digitally processed to form an MR image.

An RF transmit coil emits the $B_1$ field in an imaging region of interest when driven by a computer controlled RF transceive unit. A whole body birdcage RF body coil is commonly equipped in most commercial MRI systems. However, the large size of this RF coil produces a lower signal to noise ratio (SNR) if it is also used for reception, mainly because of its greater distance from the signal generating tissues being imaged. Instead, dedicated and conformal RF coils are often used for reception to enhance the SNR highly desirable in MRI. These dedicated RF coils, which can be volumetric type of RF coils or multi-element RF coil arrays, are specially designed to be placed near to or conform to the anatomical part or shape that is of interest. Hence, the noise that is received by these dedicated RF coils is predominantly from the dielectric samples and thus the amount of noise received will dramatically be reduced and SNR increased.

Although volumetric type of RF coils or multi-element RF coil arrays can be used, RF coil arrays, such as those described in U.S. Pat. No. 4,825,162, assigned to General Electric Company, have become more desirable. This is primarily because RF coil arrays can achieve higher SNR as compared to volumetric type of RF coils. They can be used for partial parallel imaging applications to reduce MR imaging time. RF coil arrays can be also used to perform RF field focusing, which can increase the quality of image obtained for local regions of interest, as described in International patent application WO2006094354. Lastly, RF coil arrays can be used for partial parallel transmission techniques such as Transmit SENSE [Katscher et al, Magn Reson Med 49(1) pg 144-150, 2003], which can potentially ameliorate high-field RF inhomogeneity effects.

Regardless of the many advantages that can be gained from using multi-element RF coil arrays, one common criterion in designing RF coil arrays is that some form of mutual decoupling schemes has to be incorporated to decouple the coil elements. A multi-element RF coil array usually suffers from strong mutual coupling between individual coil elements and some of the undesirable effects include difficulty in tuning, reduced SNR and RF field distortion causing image artefacts. Hence, minimizing mutual coupling is vitally important.

A number of methods have been suggested to minimize mutual coupling. Examples include a counter wound inductor decoupling method described in "A Novel 8-Channel Transceive Volume-Array for a 9.4 T Animal Scanner" by Ewald Weber, Bing Keong Li, Feng Liu, Yu Li, Peter Ullmann, Hector Sanchez and Stuart Crozier, Proc. of the 16$^{th}$ Annual Meeting of ISMRM, 2008; pp 151, the overlapping of adjacent coils, as described for example in U.S. Pat. No. 4,825,162, and the use of low input impedance pre-amplifiers and employing capacitive decoupling networks, as described in U.S. Pat. No. 7,091,721.

There are some constraints, however, in using these decoupling methods. The overlapping of adjacent coils sacrifices the area of coverage, lumped-element decoupling networks have limitations on their decoupling power and the use of low input impedance preamplifiers can limit power transfer and limit the use of the phased array coils to receive only (i.e not suitable for transceive operation).

SUMMARY OF THE PRESENT INVENTION

The present invention seeks to substantially overcome, or at least ameliorate, one or more disadvantages of existing arrangements.

In a first broad form the present invention seeks to provide a coil arrangement for use in a magnetic resonance imaging system, the imaging system being for generating a magnetic imaging field in an imaging region, the coil arrangement including at least three coils for at least one of transmitting, receiving or transceiving an electromagnetic field, each coil being provided on a coil geometry and being substantially orthogonal.

Typically the coil arrangement includes a coil support for supporting the coils, the coil support having a surface shape corresponding to the coil geometry.

Typically the coil geometry is determined depending on the imaging to be performed.

Typically the coil geometry conforms to a shape of at least a part of a subject to be imaged.

Typically the coil geometry is rotationally symmetric about a coil geometry axis.

Typically the coils are elliptical.

Typically each coil is aligned with a respective one of three orthogonal planes.

Typically the coils are provided circumferentially spaced around a coil geometry axis.

Typically the coils are azimuthally spaced by 120°.

Typically the coils are aligned at an angle to a coil geometry axis.

Typically the coils are aligned at an angle of approximately 35.3° to the coil geometry axis.

Typically the coil geometry is at least one of:
a) spherical;
b) hemispherical;
c) cylindrical;
d) conical; and,
e) ellipsoidal.

Typically each coil being provided at an intersection between the coil geometry and the orthogonal planes.

Typically the coil arrangement includes a mutual decoupling means for mutually decoupling the coils.

Typically, in use, the coils are aligned at an angle offset to an imaging field direction.

Typically, in use, the coils are provided at an angle of approximately 54.7° to an imaging field direction.

Typically the coils are arranged to reduce mutual coupling between the coils.

Typically the coil arrangement is for use in imaging by modulating/encoding a transmitted or received electromagnetic field.

A coil arrangement for use in a magnetic resonance imaging system, the imaging system being for generating a magnetic imaging field in an imaging region, the coil arrangement including:
a) a coil support; and,
b) at least three coils for at least one of transmitting, receiving or transceiving an electromagnetic field, the coils being supported by the coil support and being substantially orthogonal.

Typically the coil support has a surface shape corresponding to a coil geometry.

In a second broad form the present invention seeks to provide a method of determining a coil arrangement for in a magnetic resonance imaging system, the imaging system being for generating a magnetic imaging field in an imaging region, the method including:
a) determining a coil geometry;
b) arranging three orthogonal planes so that each of the planes intersects the coil geometry; and,
c) determining a coil arrangement for each of three coils in accordance with an intersection of a respective plane with the coil geometry.

Typically the method includes determining the coil geometry in accordance with a shape of at least a part of a subject to be imaged.

Typically the coil geometry conforms to the shape of at least a part of a subject to be imaged.

Typically the coil geometry is at least one of:
a) spherical;
b) hemispherical;
c) cylindrical;
d) conical; and,
e) ellipsoidal.

Typically the coil geometry is rotationally symmetric about a coil geometry axis.

Typically the method includes arranging the planes so that coils are elliptical.

Typically the method includes arranging the planes so that coils are circumferentially spaced around a coil geometry axis.

Typically the method includes arranging the planes so that the coils are azimuthally spaced by 120°.

Typically the method includes arranging the planes at an angle to a coil geometry axis.

Typically the planes are arranged at an angle of approximately 35.3° to the coil geometry axis.

BRIEF DESCRIPTION OF THE DRAWINGS

An example of the present invention will now be described with reference to the accompanying drawings, in which:—

DETAILED DESCRIPTION OF THE PREFERRED EMBODIMENTS

Figure 1:
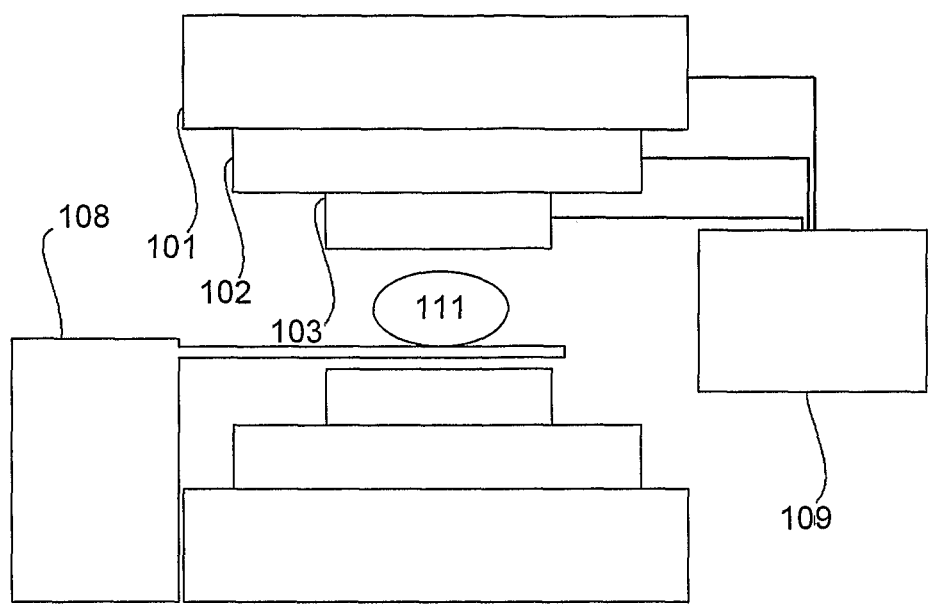
FIG. 1 is a schematic diagram of an example of an imaging system.

An example of a magnetic resonance (MR) imaging system will now be described with reference to FIG. 1.

In this example, the MR system includes a main or primary shimmed magnet 101, three principal axis gradient coils 102, a patient/sample bed 108 and MR instrumentation 109. In use, the main magnet 101 is adapted to generate a substantially homogeneous magnetic field over an imaging region 111, which contains a subject, such as at least part of a patient or sample. The subject is then exposed to an RF field, allowing MRI to be performed. The workings of these components are substantially identical to those of contemporary systems, and will not therefore be described in any further detail.

The RF field is typically transmitted and received by one or more RF coil arrays 103. In one example, separate coil arrays may be used for transmitting and receiving the RF field, whilst in another example a single transceive coil array could be used.

Figure 2:
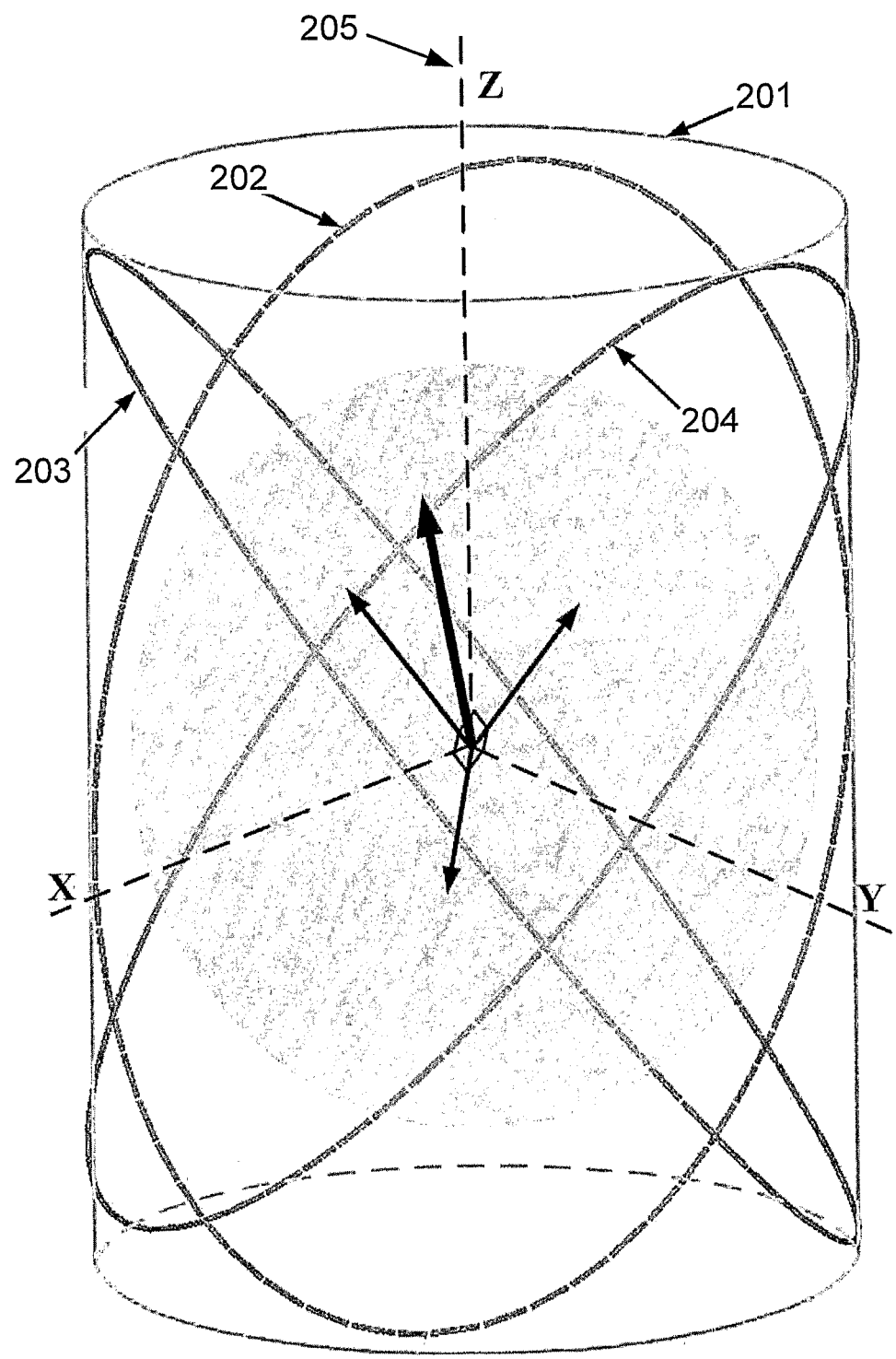
FIG. 2 is a schematic diagram of an example of a 3-element RF coil array structure.

An example of a coil array including orthogonally arranged coils (generally referred to as an orthogonality coil array) will now be described with reference to FIG. 2.

In this example, the coil array is based on a cylindrical coil geometry 201, which typically corresponds to the shape of a coil support, on which coils 202, 203, 204 are to be provided. The coils 202, 203, 204 have elliptical shapes, thereby allowing the coils 202, 203, 204 to conform to the cylindrical geometry 201 and remain mutually orthogonal. In this example, the three elliptical coils 202, 203, 204 are arranged 120° apart azimuthally and tilted to an angle of 54.7° with respect to an XY plane arranged perpendicularly to an axis 205 of the cylindrical coil geometry 201.

Accordingly, in the above described arrangement the three elliptical coils 202, 203, 204 are arranged orthogonally to one another.

Arranging the coils orthogonally reduces mutual coupling between the coils. This can be used to avoid the need for mutual decoupling schemes to be employed to decouple the RF coils, thereby simplifying the resulting MR apparatus.

In addition, orthogonal coil arrays can be positioned arbitrarily relative to the main static magnetic field ($B_0$) whilst maintaining normal operation and without any loss of efficiency and functionality. Hence, orthogonal coil arrays are capable of being used with any horizontal, vertical bore and open MRI systems. This provides clinical convenience for scanning anatomies that are not necessarily aligned with the $B_0$ field of a MRI system.

The orthogonal coil arrays can suitably be used for the design of transmit and/or receive RF coil arrays for human/animal MRI and/or magnetic resonance spectroscopy (MRS) applications.

Furthermore, in one example, the orthogonal relationship of the coils can assist in performing magic angle MRI applications, which can enhance the image intensity of structured collagen fibres, as will be described in more detail below.

Figure 3A:
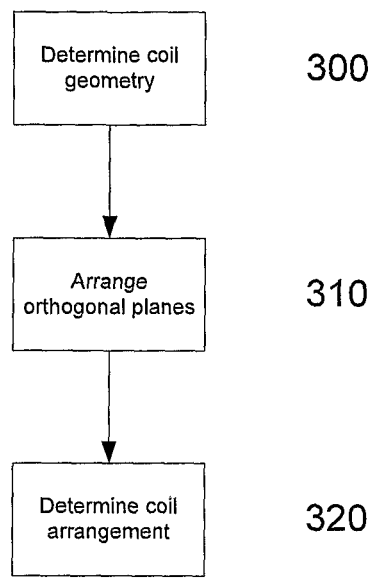
FIG. 3A is a flow chart of an example of a process for determining a coil arrangement.

An example process for determining an orthogonal coil arrangement will now be described with reference to FIG. 3A.

In this example, at step 300, a coil geometry is determined. This may be achieved in any suitable manner, and may depend for example on the design of MR apparatus in which the coil array is to be used. Typically however, the coil geometry is determined at least in part based on the intended imaging application, and in particular, is selected to conform to a shape of part of a subject to be imaged. Thus, for example, a cylindrical geometry is particularly suited for imaging limbs, as it allows the limb to be placed inside the coil support, whilst minimising the distance between the coils and the limb. However, for other body parts, different coil geometries can be used. Example coil geometries can include, but are not limited to:
spherical;
hemispherical;
cylindrical;
conical; and,
ellipsoidal.

It will be appreciated from this that the use of a cylindrical coil geometry in the above example is for the purpose of illustration only, and is not intended to be limiting. Specific example geometries and their applications will be described in more detail below.

At step 310, three orthogonal planes are arranged so that each plane intersects the coil geometry, allowing the coil arrangement to be determined at step 320, with each coil location being based on the intersection of a respective plane with the coil geometry.

Figure 3B:
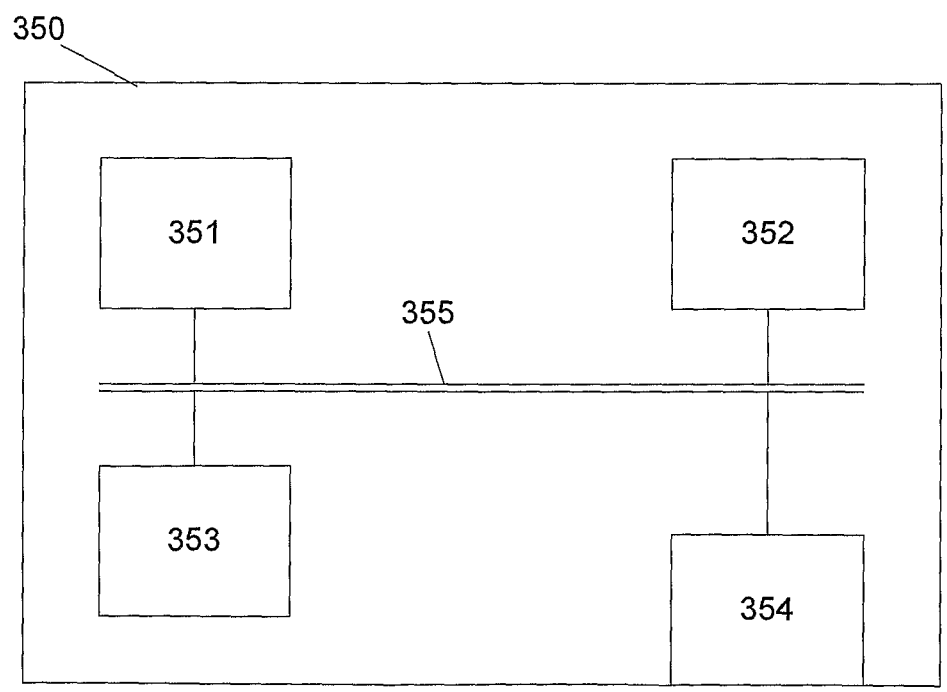
FIG. 3B is a schematic diagram of an example of a processing system.

In one example, the above described process is performed at least in part utilising a processing system, an example of which will now be described with reference to FIG. 3B.

In this example the processing system 350 includes a processor 351, a memory 352, an input/output device, such as a keyboard and mouse 353, and an optional external interface 354 coupled together via a bus 355. The optional external interface may be used to connect the processing system 350 to peripheral devices, such as communications networks, remote databases, or the like.

In use, the processor 351 typically executes applications software stored in the memory 352, to allow the processor 351 to perform required calculations and/or display coil arrangements, coil geometries and orthogonal planes, or the like. This can include, for example, allowing a user to define a coil geometry, displaying a representation of the coil geometry and associated orthogonal planes, thereby allowing the user to manipulate the representation and hence the relative position of the planes and coil geometry, and calculating resulting coil arrangements. It will be appreciated that these processes can be performed automatically, but typically involve at least some input or other control by the user.

It will therefore be appreciated that the processing system 350 may be a suitably programmed computer system, such as a laptop, desktop, PDA, computer server, or the like, although alternatively the processing system 350 may be formed from specialised hardware.

Irrespective of how the method is performed, the method provides a design technique for allowing RF coil arrays to be created that result in mutually orthogonal coils. This allows coil arrays to be designed that do not rely on any existing mutual decoupling schemes to achieve mutual decoupling of coils, and is therefore able to achieve high isolation/decoupling power. However, it will be appreciated that the orthogonality coil arrays can be used with mutual decoupling schemes to further increase isolation/decoupling power or to increase the number of coil elements that can be used in the coils.

In order to demonstrate the effectiveness of orthogonality coil arrays, example coil arrays will now be considered both in simulation and experiment.

For the purpose of this example, a combined hybrid method of moments (MoM)/finite element method (FEM) method is employed for the modelling and analysis of a 3-element orthogonality knee coil array prior to constructing a physical array.

The MoM/FEM software is commercially available from FEKO (available from EM Software & Systems-SA (Pty) Ltd of Technopark, Stellenbosch, South Africa; www.feko.info). The rational in using hybrid MoM/FEM is that MoM is well-suited for modelling complex coil structures but not as well suited to complicated biological tissue loads, due to its requirement to use either a complicated Greens' function and/or the solution of large non-sparse matrix equations necessary to accurately model the essentially lossy dielectric loads, which are time consuming. In view of this, FEM is used in place of the complicated Greens' function to model dielectric loads. Using FEM, arbitrary inhomogeneous dielectric loads can be modelled with ease. The elements used in the volume discretisation for the FEM allow for accurate geometrical representation of volumes with curved surfaces and the formulation furthermore allows for the variation in the dielectric properties from element to element.

Figure 4A:
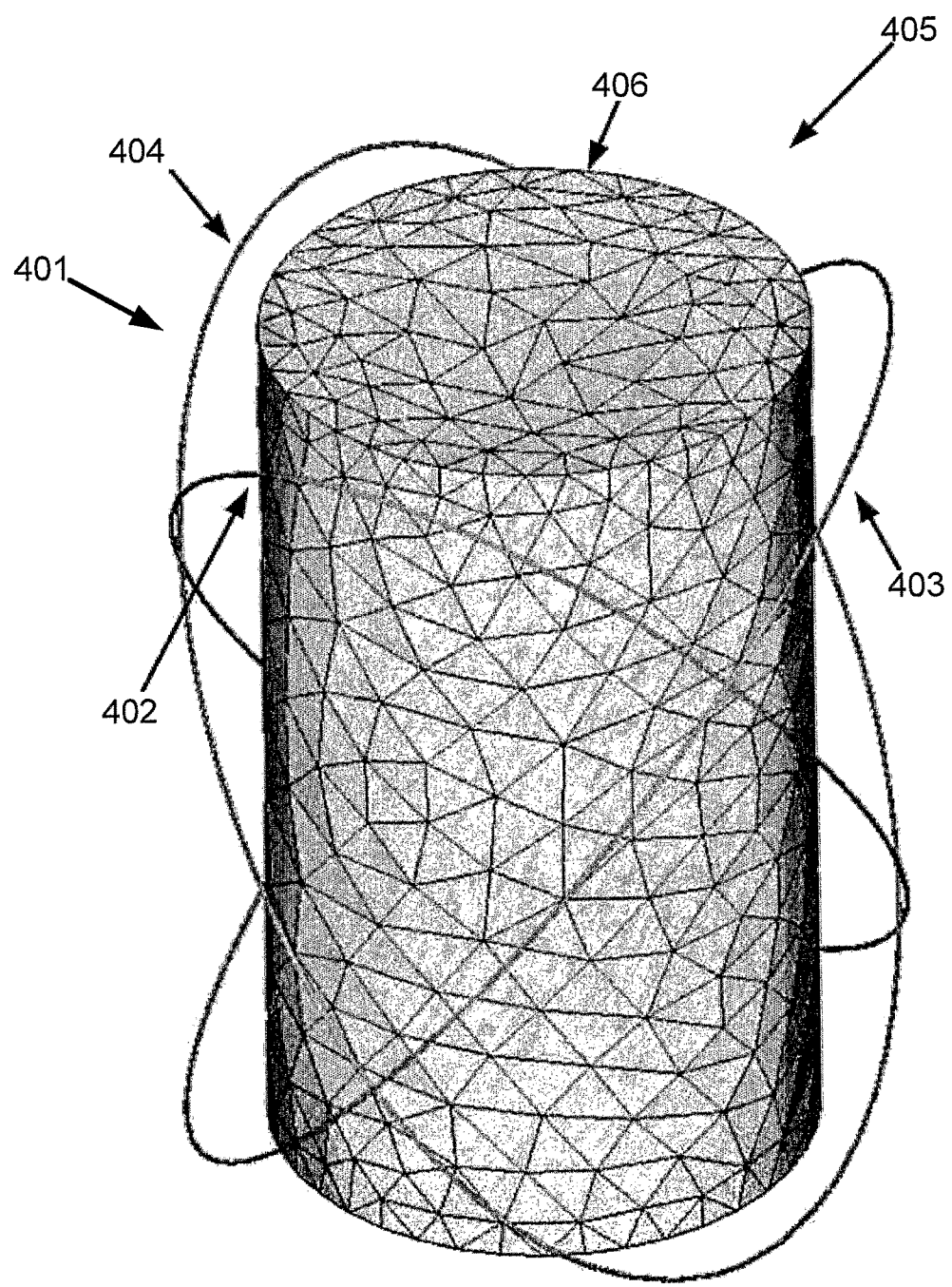
FIG. 4A is a schematic diagram of a simulated example of a 3-element orthogonality knee coil array loaded with a homogenous cylindrical phantom.
Figure 5A:
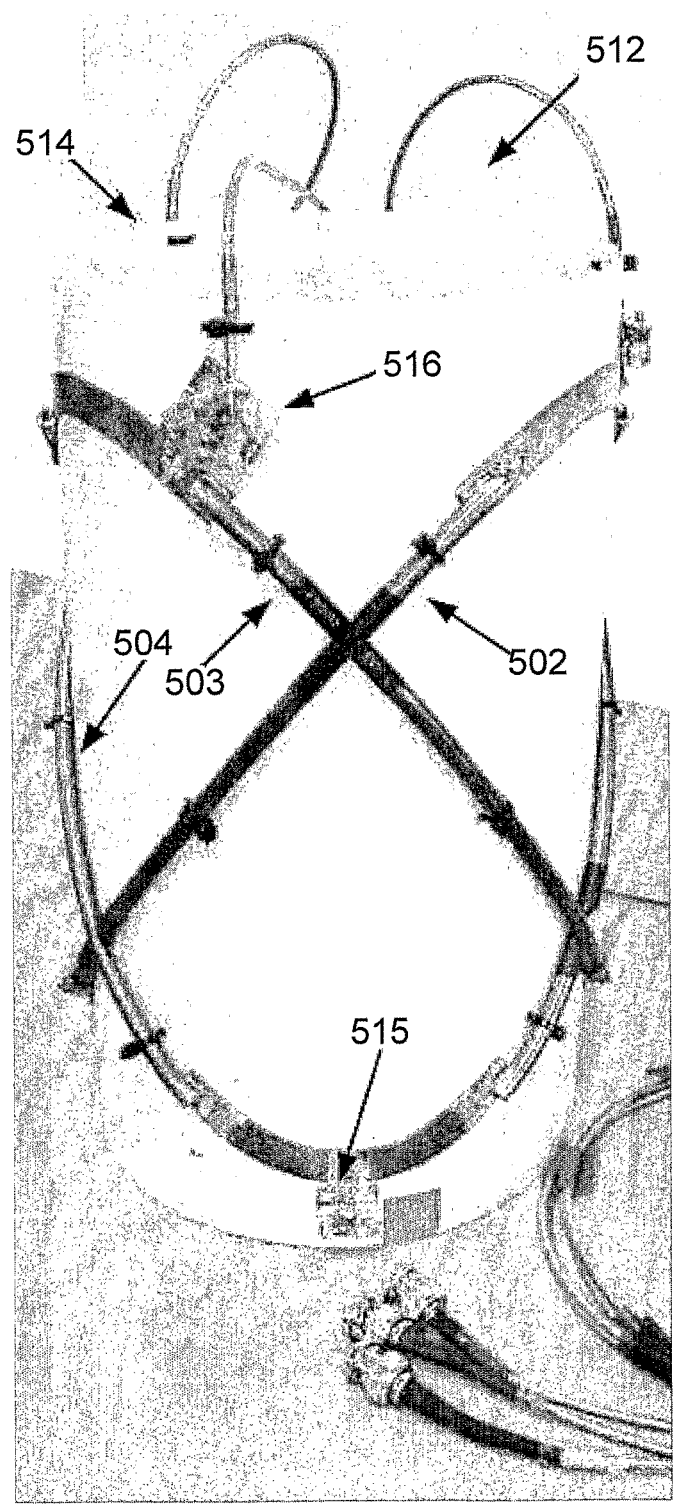
FIG. 5A is a picture of an example of a 3-element orthogonality knee coil array.

An example modelled 3-element orthogonality knee coil array is shown in FIG. 4A, with a constructed coil array being shown in FIG. 5A. In this example, the knee coil array 405 is loaded with a homogenous cylindrical phantom 406, 140 mm in diameter, with dielectric properties of $\sigma$=0.6 S/m and $\in_r$=48.6, which approximately resemble a human limb.

The 3 elliptical coil elements 402, 403, 404, are located in a respective diametric plane of the cylindrical coil geometry 401 with a diameter of 160 mm and height of 230 mm. For the coil elements 402, 403, 404 to conform to this cylindrical coil geometry 401, each elliptical coil element 402, 403, 404 measures 160 mm for it minor axis while the major axis measures approximately 280 mm. The coils are spaced equi-angularly around the cylindrical coil geometry 401 with the azimuthal angle between the nearest neighbouring coils being 120° and tilted at 54.7° as discussed previously. Three distributed capacitors are inserted around the coil element for tuning the coil element to resonate at 85 MHz and matching it to system impedance of 50Ω.

Figure 4B:
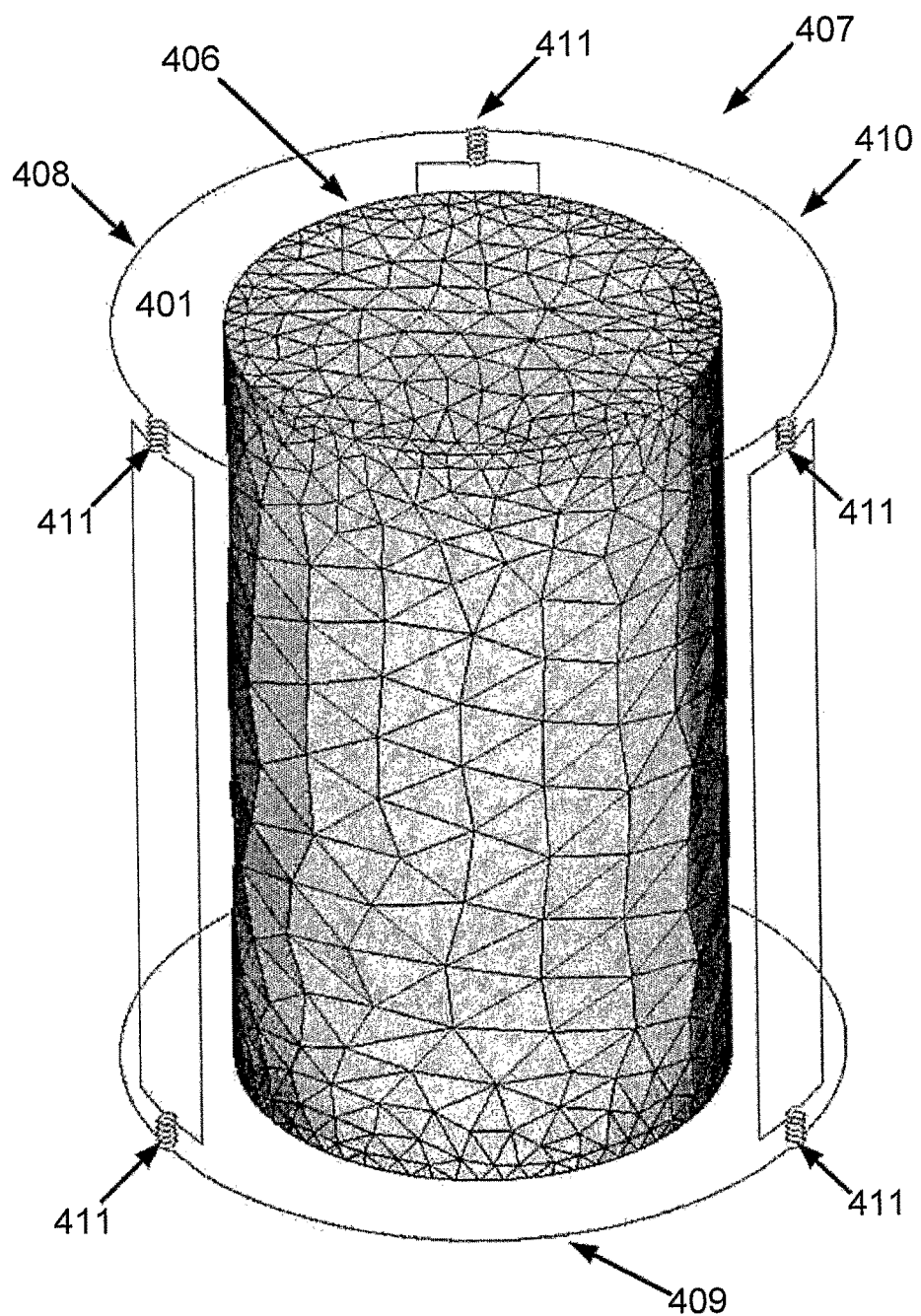
FIG. 4B is a schematic diagram of a simulated example of a conventional 3-element knee coil array loaded with a homogenous cylindrical phantom.

In order to demonstrate the orthogonality 3-element knee coil array can achieve mutual decoupling without the use of any mutual decoupling schemes and can also achieve high isolation/decoupling power, a conventional 3-element knee coil array is also designed and constructed for comparison purposes. An example modelled conventional 3-element knee coil array is shown in FIG. 4B, with a constructed coil array being shown in FIG. 5B.

The conventional knee coil array 407 uses a counter wound inductor method, described in "A Novel 8-Channel Transceive Volume-Array for a 9.4 T Animal Scanner" by Ewald Weber, Bing Leong Li, Feng Liu, Yu Li, Peter Ullmann, Hector Sanchez and Stuart Crozier, Proc. of the 16$^{th}$ Annual Meeting of ISMRM, 2008; pp 151, and as also described in co-pending patent application AU2007901587, to achieve mutual decoupling. The coil elements 408, 409, 410 of the conventional knee coil array 407, are similarly located in a respective diametric plane of the cylindrical coil geometry 401 with a diameter of 160 mm and height of 230 mm. Each coil element measured 147 mm in width and 230 mm in height. The coils 408, 409, 410 are spaced equi-angularly around the cylindrical space with the azimuthal angle between the nearest neighbouring coil being 120° and is loaded with a homogenous cylindrical phantom 406. Counter wound inductors 411 are also provided as described in co-pending patent application AU2007901587 incorporated into each coil element 408, 409, 410, to perform mutual decoupling between the coil elements.

Once both the orthogonality knee coil array 405 and the conventional knee coil 407 have been modelled, MoM/FEM is utilized to first check if mutual couplings between coil elements have been minimized. This is verified by calculating the $S_{11}$, $S_{21}$ and $S_{31}$ responses.

As noted, for the orthogonality knee coil array 405, no dual minimum or a 'splitting' of the resonant frequency as explained in U.S. Pat. No. 4,825,162 can be observed in the calculated $S_{11}$, $S_{21}$ and $S_{31}$ responses. Persons skilled in the field will understand that 'splitting' of the resonant frequency will appear if mutual couplings between coil elements are not minimized.

Similarly, for the conventional knee coil, $S_{11}$, $S_{21}$ and $S_{31}$ responses are calculated. However, it is noted that in this instance, a simplex optimization algorithm is employed to find the optimum number of turns each counter wound inductor 411 should have and the optimum overlapping distant between neighbouring counter wound inductors 411 should be so that no 'splitting' of the resonant frequency can be observed in the calculated $S_{11}$, $S_{21}$ and $S_{31}$ responses. Further evidence that mutual couplings have been minimized will be described in more detail below.

After verifying coil elements for both the orthogonality knee coil array and the conventional knee coil have been mutually decoupled, MoM/FEM is next employed to calculate the magnetic fields inside the cylindrical phantom 406 with an axial plane (xy plane) profile, located at the mid section. The calculated magnetic fields are then used to generate the MR images of the cylindrical phantom as described in "A Focussed, 8-element Transceive Phased Array Coil for Parallel MRI of the Chest—Theoretical Consideration" by Bing Keong Li, Feng Liu and Stuart Crozier, Magnetic Resonance in Medicine 2005; 53(6), pp. 1251-1257. In this paper it is described how the magnetic fields are calculated and how there are used to generate the MR image of the cylindrical phantom.

The simulated MR images are used for comparing with the one acquired using the constructed coil arrays, as will be described in more detail below.

Figure 5B:
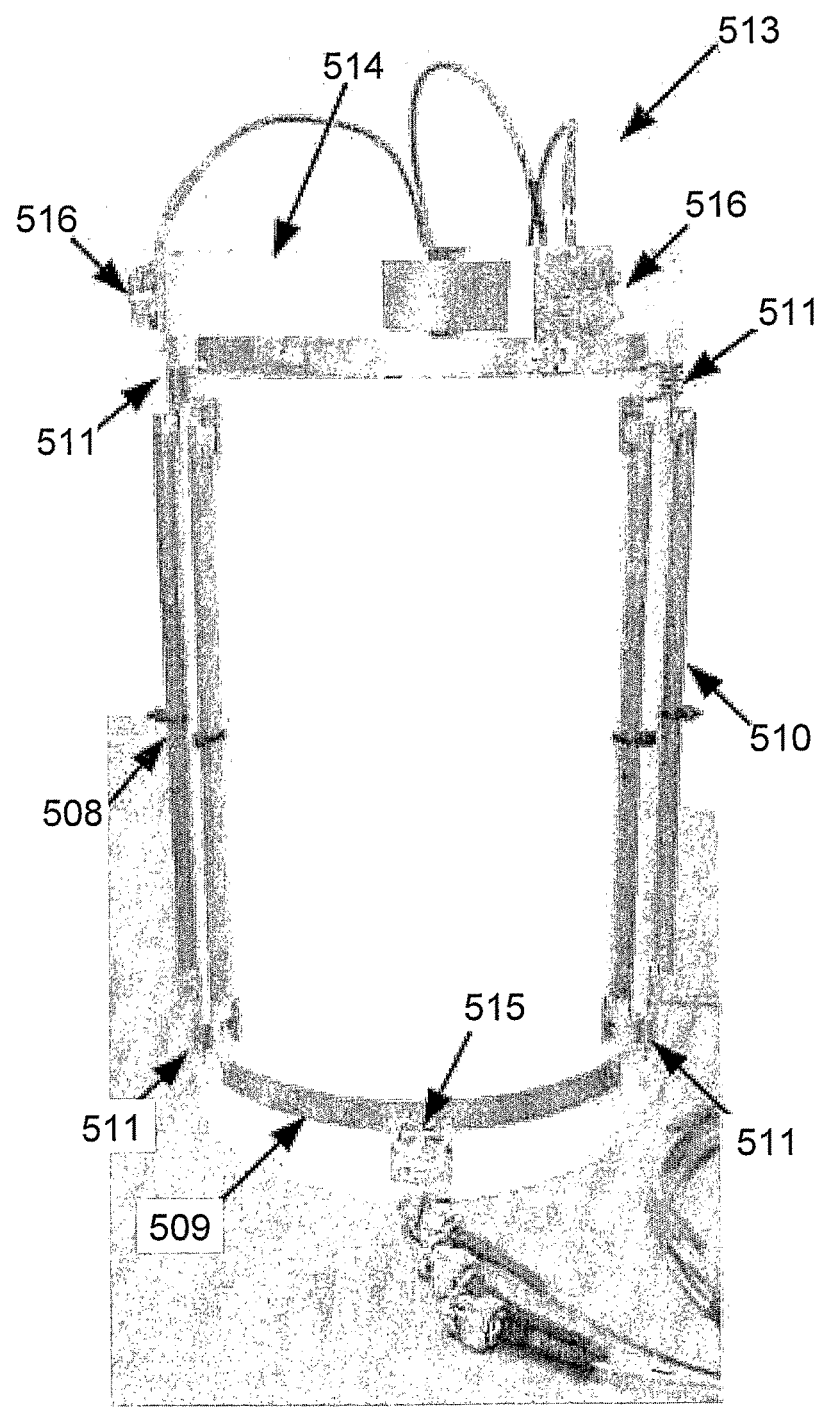
FIG. 5B is a picture of an example of a conventional 3-element knee coil array.

The 3-element orthogonality knee coil array 405 can achieve mutual decoupling without the need of additional mutual decoupling scheme and the conventional knee coil array 407 can achieve mutual decoupling by using the counter wound inductor method. Examples of constructed knee coil arrays are shown in FIGS. 5A and 5B. Both arrays 512, 513 are constructed in structure and dimensions according to how they are modelled as shown in FIGS. 4A and 4B.

In these examples, a cylindrical tube 514 made of polyvinyl chloride material, of size 160 mm in diameter and height of 270 mm is used as the support structure for coil elements 502, 503, 504, 508, 509, 510 and also for allowing dielectric samples to rest thereon. In addition, fine resolution tuning system 515 and impedance matching active decoupling system 516 are incorporated into each coil element 502, 503, 504, 508, 509, 510. Persons skilled in the art will understand these systems can be used in order to provide tuning of the coil elements to resonate at 85 MHz and matching the coil element to system impedance of 50Ω while the active decoupling system switches the knee coil arrays 512, 513 into open circuit configuration during the transmission of the 90° RF pulse (via the built-in whole body RF system).

Prior to testing the constructed knee coil arrays 512 and 513 in a Bruker S200 2 T whole-body MRI system equipped with four receiver channels, both constructed knee coil arrays were tested on the workbench for successful mutual decoupling, which is determined by inspecting the measured S-parameters between coil elements. An Agilent 2 port RF network analyser, model number 8712 ET is used for measuring the S-parameters. It should be noted that measurement of the S-parameters is performed with the constructed knee coil array 512, 513 loaded with a homogenous cylindrical phantom.

Figure 6A:
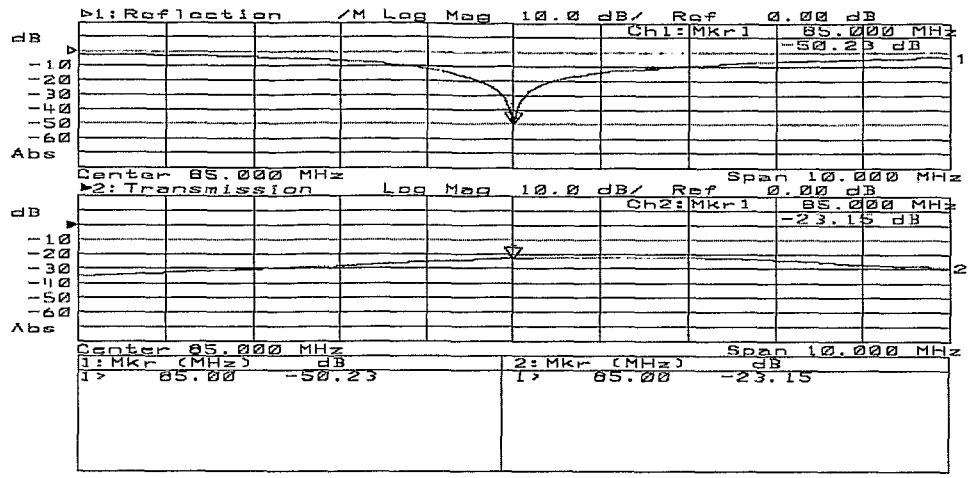
FIGS. 6A and 6B are graphs of examples of measured S-parameters for the 3-element knee coil array of FIG. 5A.
Figure 6B:
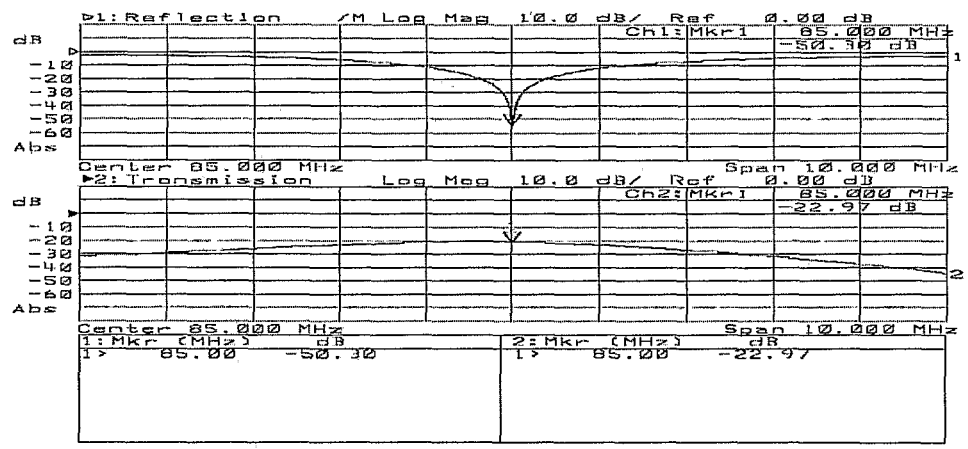
Figure 7A:
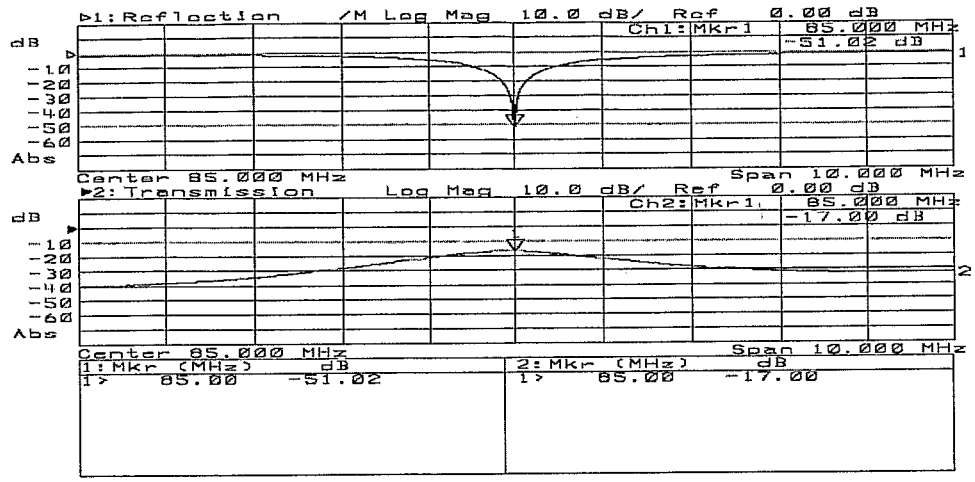
FIGS. 7A and 7B are graphs of examples of measured S-parameters for the conventional 3-element knee coil array of FIG. 5B.
Figure 7B:
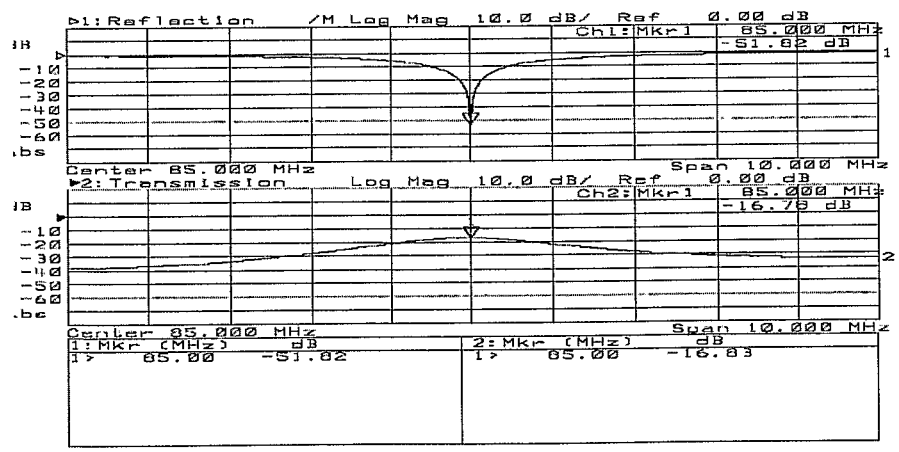

FIGS. 6A and 6B show are the measured S-parameters for the 3-element orthogonality knee coil 512 while FIGS. 7A and 7B are the measured S-parameters for the conventional 3-element knee coil 513. In FIGS. 6A and 7A, "Coil 1" is connected to the reflection port, while "Coil 2" is connected to the transmission port of an analyzer, whereas in FIGS. 6B and 7B, "Coil 1" is connected to the reflection port, while "Coil 3" is connected to the transmission port of an analyzer. Table 1 below outlines the coil combinations for each measurement shown in FIGS. 6A, 6B, 7A, 7B. In each case the measurement applies to both the knee coil arrays 512 and 513 with a 2 T field at 85 MHz using 3 channels.

TABLE 1

| orthogonality knee coil 512 | | | conventional knee coil 513 | | |
| --- | --- | --- | --- | --- | --- |
| FIG. | S11 | S21 | FIG. | S11 | S21 |
| 6A | Coil 1 | Coil 2 | 7A | Coil 1 | Coil 2 |
| 6B | Coil 1 | Coil 3 | 7B | Coil 1 | Coil 3 |

It will be noted that no "splitting" of the resonance frequency is visible in FIGS. 6A and 6B indicating that mutual couplings between coil elements 502, 503, 504 are minimised. Hence, mutual decoupling occurs naturally without the need for any mutual decoupling schemes. Likewise, FIGS. 7A and 7B also demonstrated that mutual decoupling can be achieved by using the counter wound inductor method.

It will be noted that in comparing the isolation/decoupling power between these two different designs of the 3-element knee coil array, the orthogonality knee coil array 512 can achieve higher isolation/decoupling power as compared to the conventional knee coil array 513, approximately −23 dB as compared to −17 dB. These measured S-parameters provide evidence supporting that the use of orthogonal coils can achieve higher isolation/decoupling power.

After confirming both constructed knee coil arrays 512 and 513 are mutually decoupled, they are tested in the 2 T MRI system. Three comparison MRI experiments between the orthogonality knee coil array 512 and the conventional knee coil array 513 will now be described.

Figure 8A:
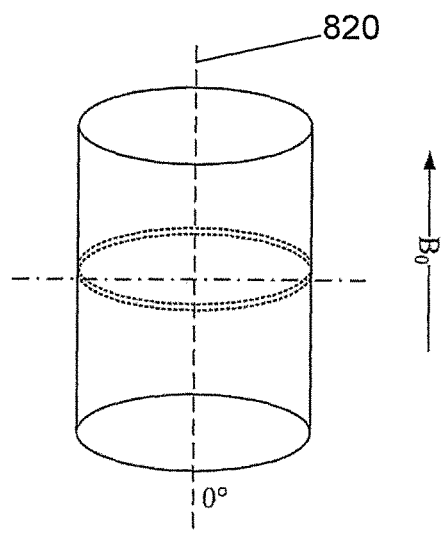
FIG. 8A is a schematic diagram of an example of the position of the knee coils arrays of FIGS. 5A and 5B relative to a $B_0$ field.

The first experiment is to show the orthogonality knee coil array 512 is invariant to the direction of the main static magnetic field $B_0$ of the MRI system and can be arbitrarily positioned in a MRI system without losing any functionality. In this experiment, a homogenous cylindrical phantom having the same dimensions and dielectric properties as the modelled cylindrical phantom 406 is imaged. The orthogonality knee coil array 512 and the conventional knee coil array 513 are firstly positioned with a geometry axis 820 corresponding to t axis of the cylindrical tube 514 aligned with the direction of the $B_0$ field as illustrated in FIG. 8A.

Using a Fast Low Angle Shot (FLASH) imaging pulse sequence with TR=100 msec, TE=9.1 msec and NEX=1, three axial slice images located at the mid section of the cylindrical phantom are acquired in parallel by each coil element of the two constructed knee coil arrays 512, 513. The parallel received MR images are thereafter combined using a sum-of-square method, forming a composite image of the cylindrical phantom.

Figures 8B, 8D:
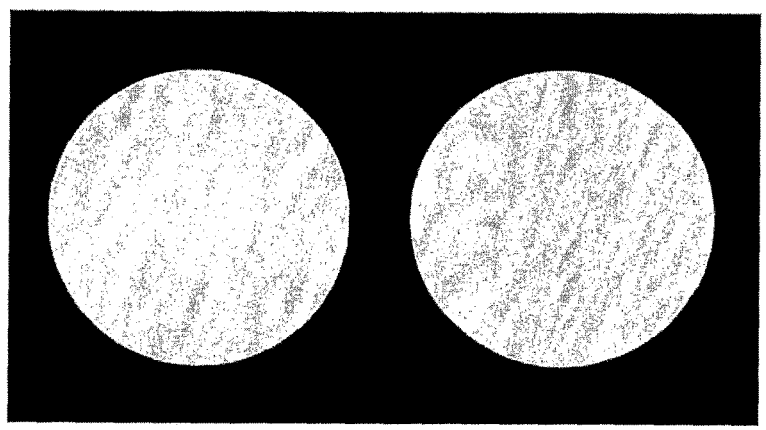
FIGS. 8B and 8C are diagrams of example experimentally acquired axial-plane MR images of a cylindrical phantom for the 3-element knee coil arrays of FIGS. 5A and 5B respectively.
FIGS. 8D and 8E are diagrams of example simulated MR images of the cylindrical phantom arrangement of FIGS. 4A and 4B respectively.
Figures 8C, 8E:
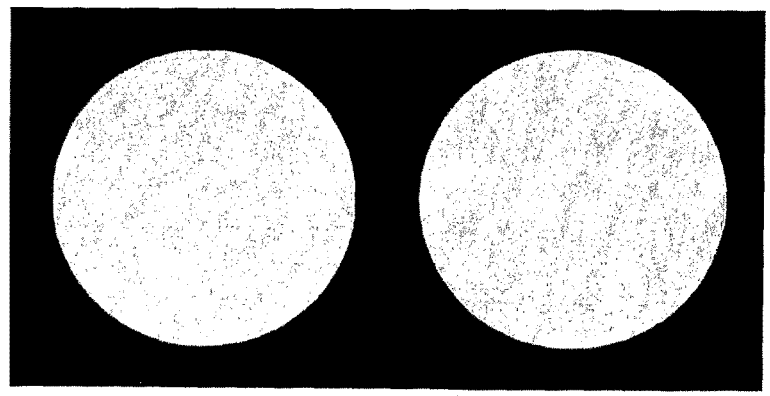

FIG. 8B shows the acquired MR image of the cylindrical phantom using the orthogonality knee coil array 512 while FIG. 8C is the MR image acquired using the conventional knee coil array 513. Depicted in FIGS. 8D and 8E are the simulated MR images of the modelled cylindrical phantoms. It can be seen that the simulated MR images can provide very accurate results similar to the images acquired experimentally.

It will be noted that, more importantly, the MR images acquired using the orthogonality knee coil array 512 show a high level of homogeneity similar to the MR image of FIG. 8C acquired using the conventional knee coil array 513. This is an indication that although coil elements 502, 503, 504 of the orthogonality knee coil array 512 are arranged to loop around the cylindrical space defined by the tube 514 and tilted at an angle relative to the $B_0$ field and hence the sample, they do not suffer any degradations in terms of efficiency and functionality as compared to the conventional techniques of using surface coils that have conducting surfaces facing flat to the sample under imaging, as in the case of the coil elements 508, 509, 510 that are used in the conventional knee coil array 513.

In addition, the measured SNRs obtained from FIGS. 8B and 8C are approximately 75.871 for the orthogonality knee coil array 512 and 72.585 for the conventional knee coil array 513, which indicate the orthogonality knee coil array 512 can provide a higher SNR.

Figures 9A, 9B:
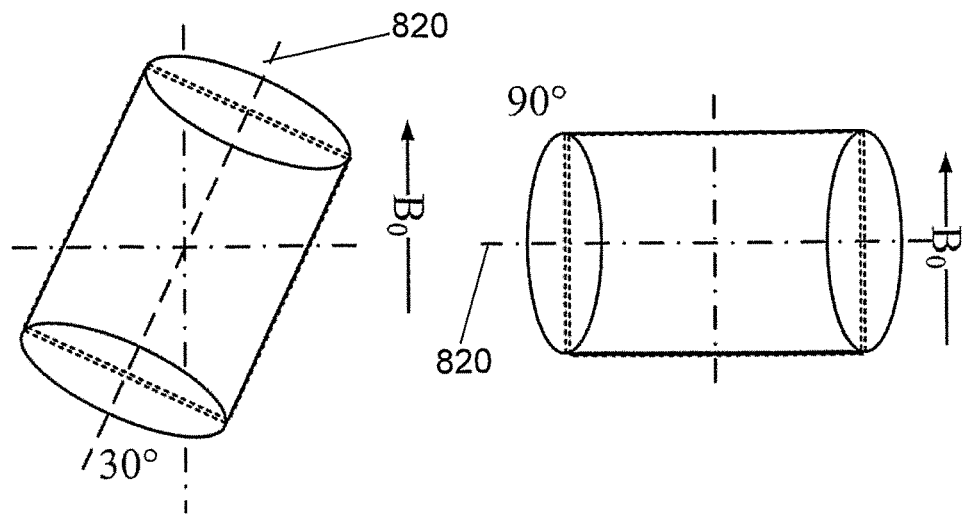
FIGS. 9A and 9B are schematic diagrams of examples of the position of the knee coils arrays of FIGS. 5A and 5B at angles of 30° and 90° relative to a $B_0$ field.

Following this experiment, two additional MR imaging processes are performed using the cylindrical phantom. Firstly the constructed knee coils 512, 513 and the cylindrical phantom are arranged with the geometry axis 520 at an angle of 30° to the direction of the $B_0$ field as illustrated in FIG. 9A. Secondly, the constructed knee coils 512, 513 and the cylindrical phantom are arranged with the geometry axis 520 at an angle of 90° to the direction of the $B_0$ field as illustrated in FIG. 9B. FLASH imaging pulse sequence with same imaging parameters as described earlier is used to acquire MR images of the cylindrical phantom at these two different positions.

Figures 9C, 9D:
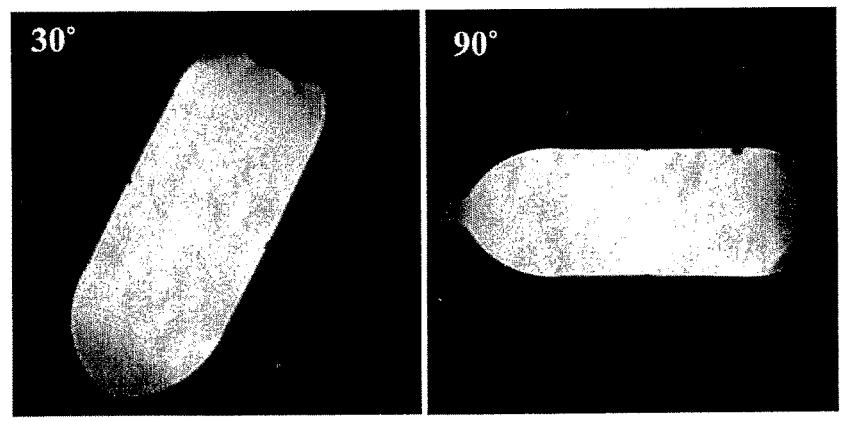
FIGS. 9C and 9D are diagrams of example experimentally acquired coronal and axial slice MR images of the cylindrical phantom using the knee coil array of FIG. 5A positioned at 30° and 90°, respectively.
Figures 9E, 9F:
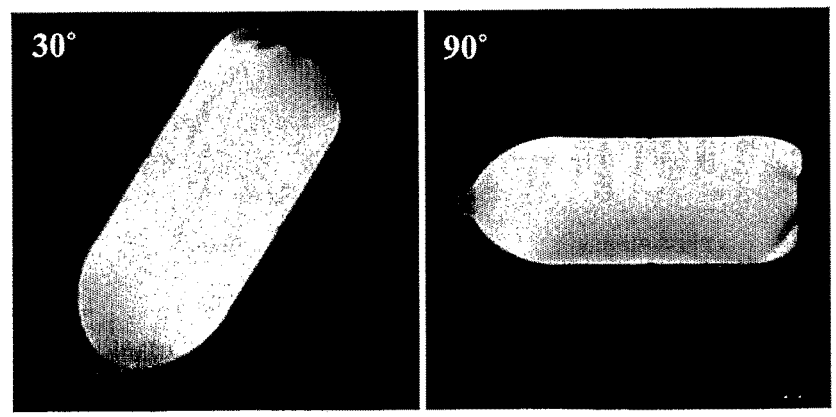
FIGS. 9E and 9F are diagrams of example experimentally acquired coronal and axial slice MR images of the cylindrical phantom using the knee coil array of FIG. 5B positioned at 30° and 90°, respectively.

FIGS. 9C and 9D show acquired coronal and axial slice images of the cylindrical phantom using the orthogonality knee coil array 512, while FIGS. 9E and 9F are corresponding image slices of the cylindrical phantom acquired using the conventional knee coil array 513. In comparing FIGS. 9C and 9E, at the 30° angle, it can be seen that the MR image of FIG. 9E, acquired using the conventional knee coil array 513, is failing to maintain homogeneity. In contrast, the MR image of FIG. 9C acquired using the orthogonality knee coil array 512 can still provide high homogeneity at this position. This is further elucidated by the measured SNRs of these two MR images, which are 75.122 using the orthogonality knee coil array 512 and 61.446 using the conventional knee coil array 513.

For the experiment with the constructed knee coil arrays 512, 513 at the position of 90°, comparing FIGS. 9D and 9F, it is evident that the MR image of FIG. 9F, acquired using the conventional knee coil array 513 has failed to operate normally. An arc of dark area at the lower half of the image has distorted the image. However, the MR image of FIG. 9D acquired using the orthogonality knee coil array 512 shows that a high homogeneity is still achievable. In addition, the measured SNRs of these two MR images are 60.774 using the orthogonality knee coil array 512 and 31.709 using the conventional knee coil array 513.

From these two experimental results, it will be noted that the orthogonality knee coil array 512 demonstrates invariance to the direction of the $B_0$ field. It can be arbitrarily positioned in a MRI system and does suffer any degradation in terms of efficiency and functionality. It is also important to note that for the experiment where the knee coil arrays 512, 513 are positioned perpendicular (90°) to the direction of the $B_0$ field, the experiment is to mimic the scenario where the knee coil arrays 512, 513 will be used in an open magnet MRI system. The results obtained for this particular experiment highlight that orthogonality coil arrays can suitably be used in an open magnet MRI system. The measured SNRs using the orthogonality knee coil array 512 show consistencies regardless of how it is positioned with respect to the direction of the $B_0$ field, thus providing further evidence that the orthogonal coil arrangement can suitably be used with all current MRI systems.

The MRI experiments on the cylindrical phantom clearly show benefits of the orthogonal coil arrangement. To further demonstrate the benefits, further testing on human imaging will now be described. In this example, imaging of the left knee of a healthy male volunteer with consensual approval was undertaken. The left knee of the healthy male volunteer was imaged using both knee coil arrays 512, 513.

Figure 10A:
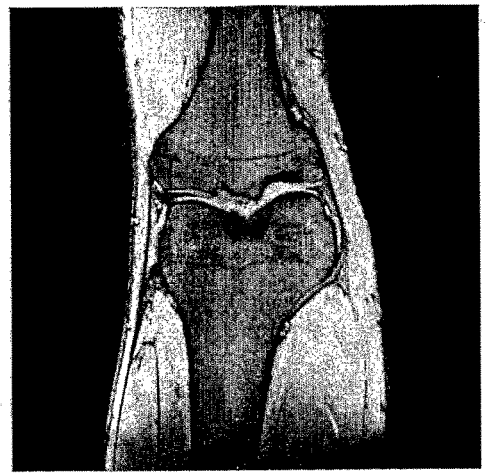
FIGS. 10A and 10B are diagrams of examples of experimentally acquired coronal and saggital slice MR images of a male volunteer's left knee using the knee coil array of FIG. 5A.
Figure 10C:
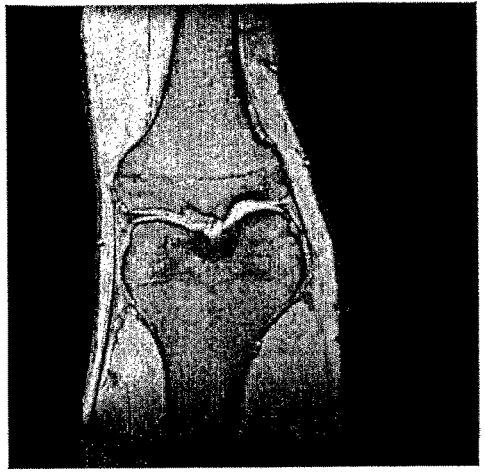
FIGS. 10C and 10D are diagrams of examples of experimentally acquired coronal and saggital slice MR images of a male volunteer's left knee using the conventional knee coil array of FIG. 5B.
Figure 10B:
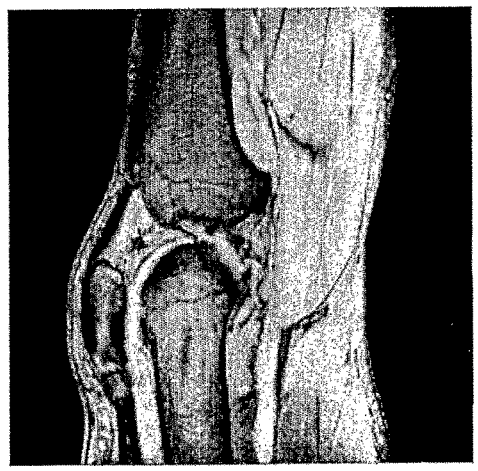
Figure 10D:

FIGS. 10A and 10B show coronal and saggital slice images of the left knee acquired with the orthogonality knee coil array 512 while FIGS. 10C and 10D show corresponding images acquired with the conventional knee coil array 513. In comparing these images, it will again be noted that the orthogonality knee coil array 512 acquires higher quality MR images of the human knee comparable to the conventional knee coil array 513, which further supports that having coil elements looped around the cylindrical coil geometry and tilted at an angle, as described above, will not cause any degradations to the efficiency and functionality of the orthogonality knee coil array 512. It should be noted that no decoupling scheme is needed by the orthogonality knee coil array 512 for acquiring these high quality MR images. Hence, coil arrays design with orthogonal coils can be greatly simplified and further allow easy modifications to the coil arrays so that they can be operated in either transmit-only, receive-only or transceive modes.

For a third experiment, the benefit of the orthogonality knee coil array 512 for magic angle MRI application is investigated. In MRI, it is well recognized that the magic angle phenomenon can increase the signal intensity of collagen fibres when they are placed at the "magic angle" of 54.74° (usually approximated to 55°) to the $B_0$ field. In practice, to perform magic angle MRI application, the sample under imaging and the RF coil are positioned at the magic angle. However, with the earlier MRI experiment on the cylindrical phantom, it is shown that using conventional RF coil loss of SNR is unpreventable if they are positioned away from the direction of the $B_0$ field. However, this is not the case for the orthogonality knee coil array 512 designed as described above. Hence, it is recognised that using the coil arrays described above can have further benefits in magic angle applications.

Figure 11A:
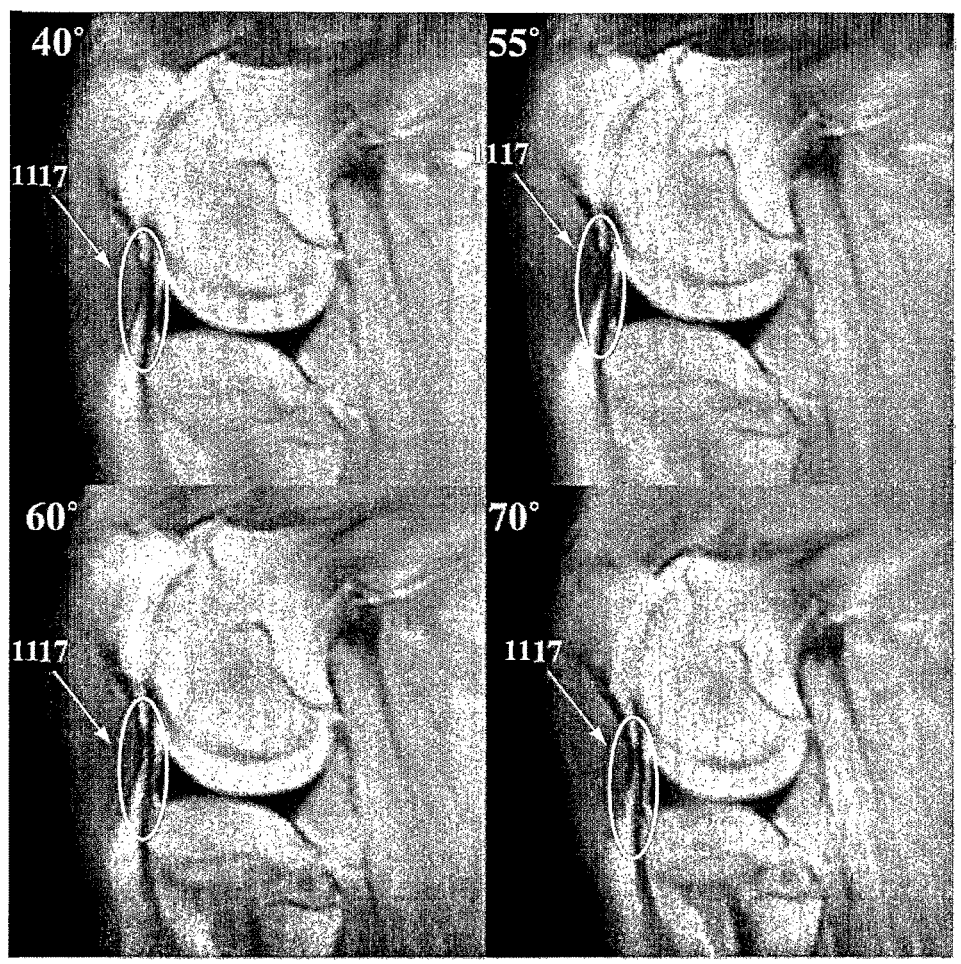
FIG. 11A is a diagram of an example of experimentally acquired MR images of an adult pig's knee with the knee coil array of FIG. 5A positioned at 40°, 55° 60° and 70° with respect to the $B_0$ field.
Figure 11B:
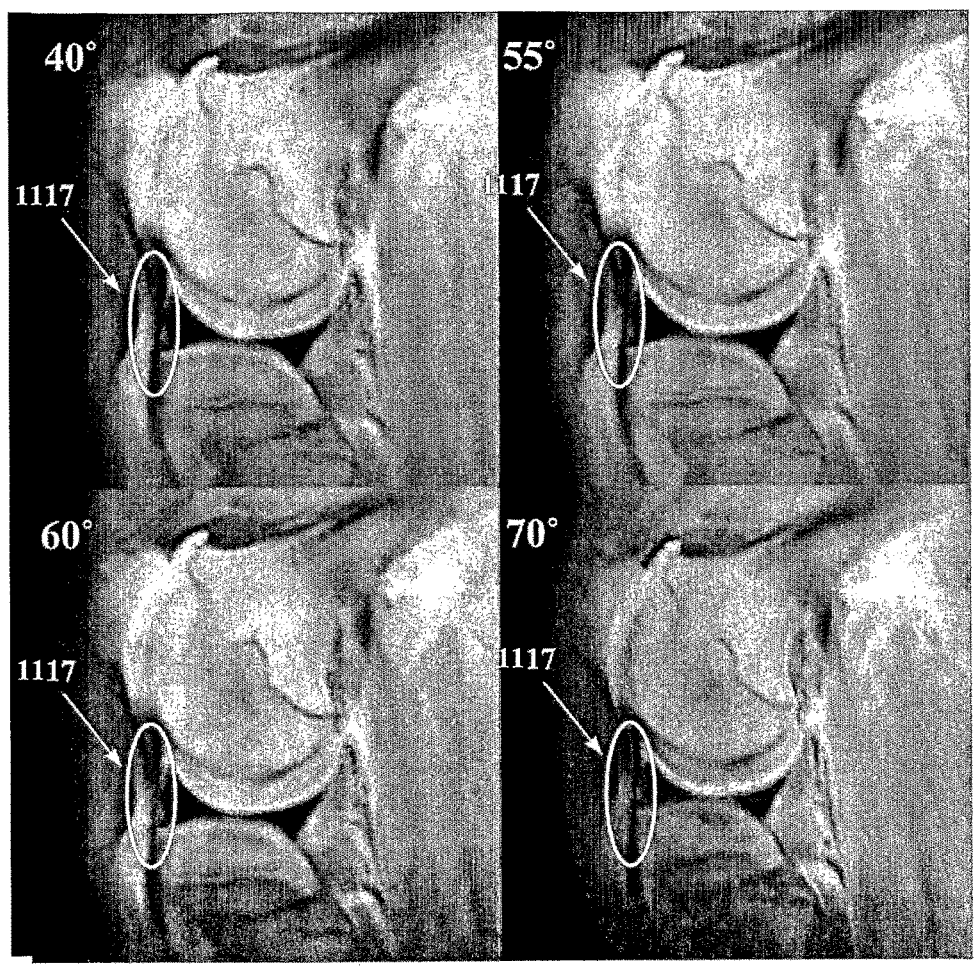
FIG. 11B is a diagram of an example of experimentally acquired MR images of an adult pig's knee with the conventional 3-element knee coil array of FIG. 5B positioned at 40°, 55° 60° and 70° with respect to the $B_0$ field.

To demonstrate this, magic angle MRI experiments on an adult pig knee using both knee coil arrays 512, 513 positioned at 40°, 55°, 60° and 70° relative to the $B_0$ field are undertaken. MR images of the pig knee acquired at these different angles using the orthogonality knee coil array 512 are shown in FIG. 11A, while FIG. 11B depicts the images acquired using the conventional knee coil array 513.

Figure 12:
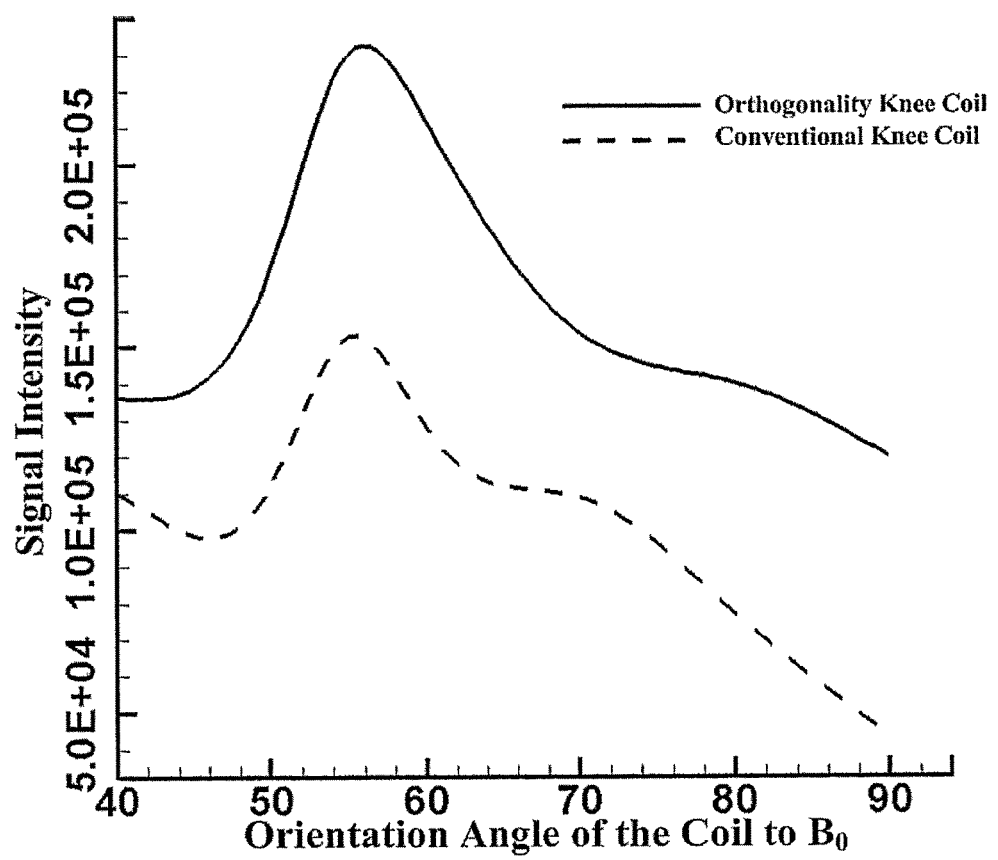
FIG. 12 is a graph of measured signal intensity plots of the patellar ligament for the images of FIGS. 11A and 11B.

The patellar ligament encircled by the white line 1117 is used to show the magic angle phenomenon. In comparing the four images of FIG. 11A, it can be seen that the patellar ligament 1117 taken at 55° appears brighter than those taken at 40°, 60° and 70°. This effect is also apparent with the four images of FIG. 11B. To better show the magic angle phenomenon, the signal intensity of the patellar ligament 1117 at these positions is measured and plotted as shown in FIG. 12. On inspecting the signal intensity plot of FIG. 12, it can be seen that starting with the position at 40°, the signal intensity of the patellar ligament 1117 increases gradually peaking at 55°, which is the magic angle and subsequently decreases when positioned beyond the magic angle. This magic angle effect can be seen when using both knee coil arrays 512, 513. However, in comparing the measured signal intensity of both knee coil arrays 512, 513, it will be noted that the orthogonality knee coil array 512 can provide higher signal intensity. The measured signal intensity at the magic angle of 55° using the orthogonality knee coil array 512 is 2.3e5 while using the conventional knee coil array 513 is 1.53e5. An improvement of 53.33% can be gained from using the orthogonality knee coil array 512 designed as described above. This is an indication that the above described design process and the resulting orthogonality coil arrangements can therefore provide the additional benefit of improving magic angle MRI applications, enhancing MR images of collagen fibres.

The above described examples focus on a coil geometry corresponding to a cylindrical space. However, the techniques can suitably be applied to the design of other shapes, and in particular other shapes designed to conform to the shape of a part of the subject to be imaged. Specific examples will now be described.

Figure 13A:
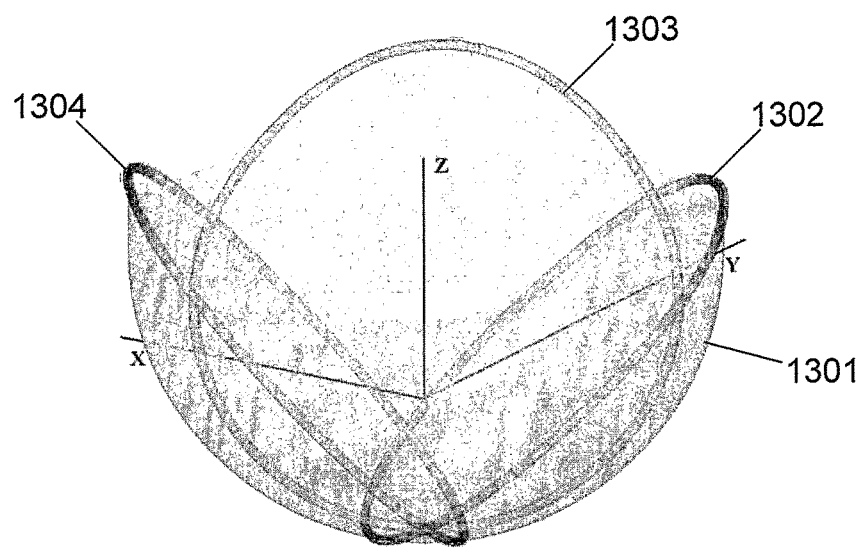
FIG. 13A is schematic diagram of an example of a 3-element orthogonality breast coil array for MRI breast imaging applications.

In the example of FIG. 13A, the above described orthogonal coil design technique is applied to the design of a 3-element breast coil array based on a half-spherical space 1301, which can be used to rest the breast on during imaging. In this example, the three coil elements 1302, 1303, 1304 are arranged 120° apart azimuthally and tilted to an angle of 54.74° with respect to an XY plane. As a result, the three coil elements 1302, 1303, 1304 are orthogonal to one another and minimum mutual coupling will exists between the coil elements as previously explained.

Figure 13B:
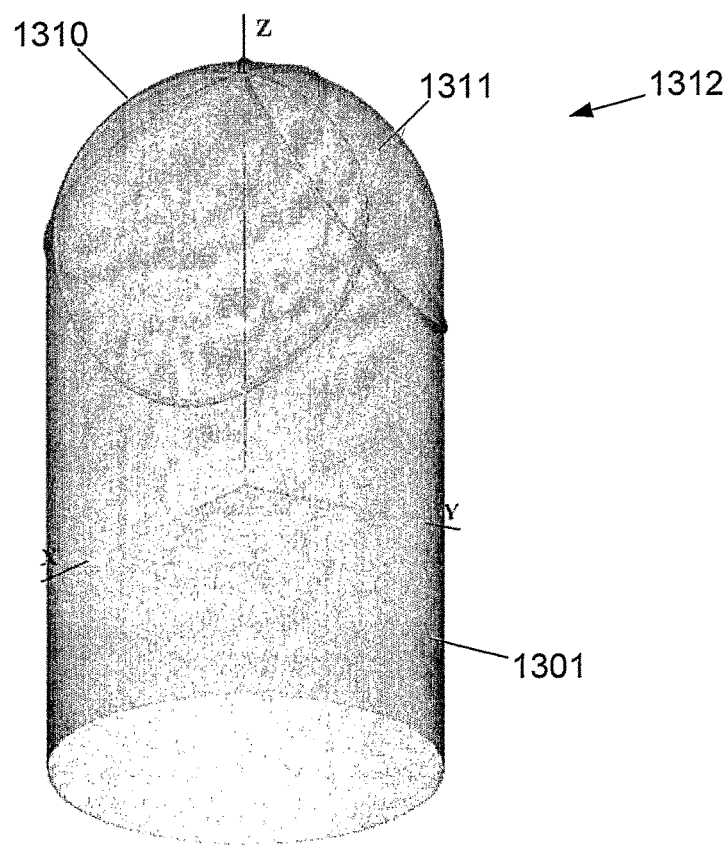
FIG. 13B is schematic diagram of an example of a 3-element orthogonality intravenous coil; and, FIG. 13C is schematic diagram of an example of a 6-element orthogonality intravenous coil.

As the orthogonality coil arrays are invariant to the direction of the applied $B_0$ field, the half-spherical coil array design can also be used for designing coil array system for unguided intravenous MRI applications where controlling of the position of a coil array system is not possible. An example of this is shown in FIG. 13B, in which a 3-element coil array 1310 is provided on a hemispherical portion 1311 of a probe 1312.

Figure 13C:
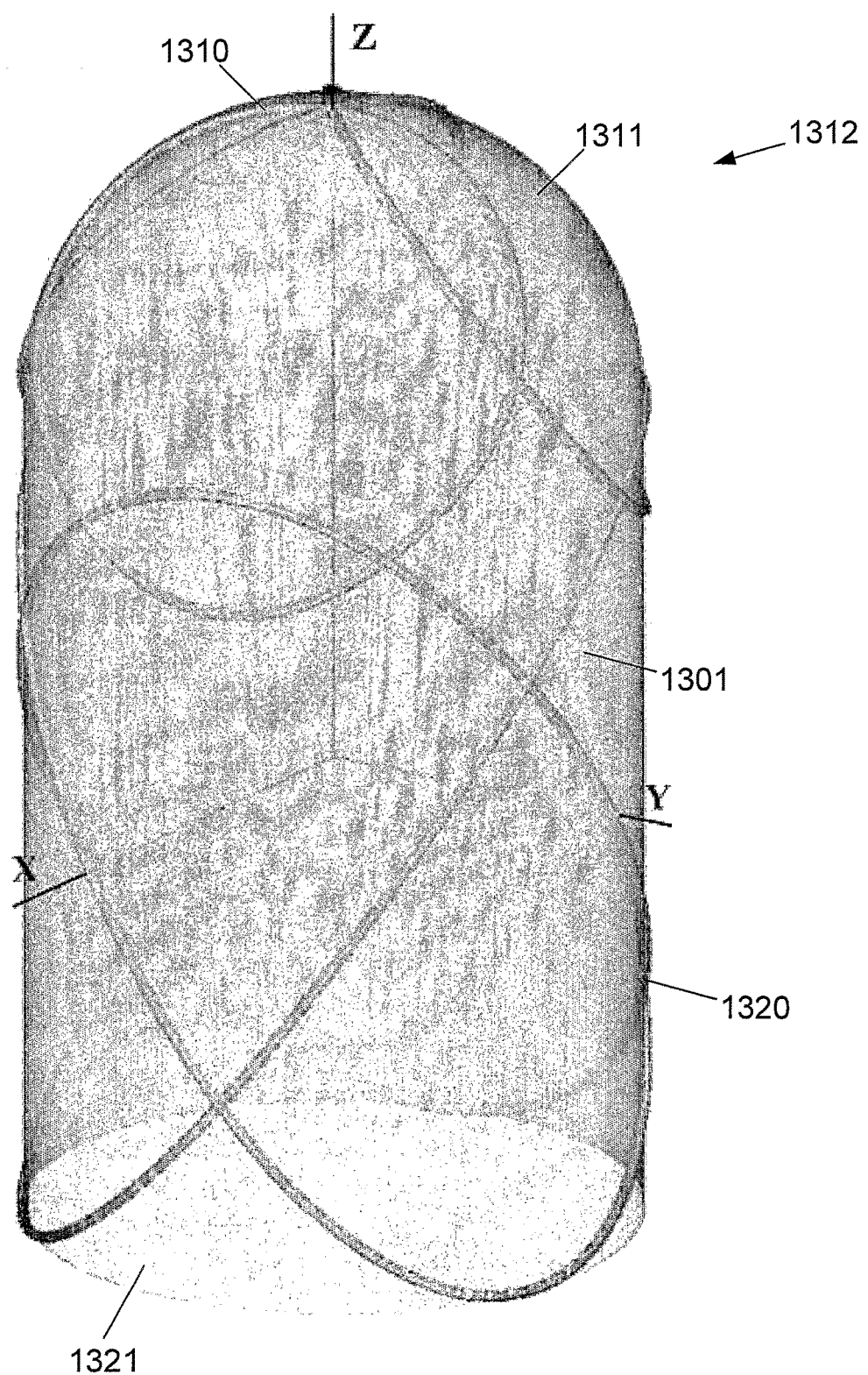

A further extension to this arrangement is shown in FIG. 13C, in which an additional 3-element system 1320 is provided on a cylindrical part 1321 of the probe 1312. It will be noted that some form of mutual decoupling scheme will be required to decouple these two separate coil systems 1310, 1320 and a possible decoupling scheme that can be used is an overlapping method as shown.

In addition, it will be noted that coil arrays designed as described above can easily be modified for multi-nucleus MR imaging due to the benefit that since mutual decoupling occurs naturally, to modify any coil array system designed for multi-nucleus MR imaging will be a matter of simply re-tuning and re-matching each coil element to resonant at the Larmor frequencies of the different nucleus of interest.

Accordingly, the above described examples highlight how coil orthogonality can be achieved, resulting in improved imaging characteristics. In one example, this is achieved so that the coils are tilted at an angle relative to a coil geometry axis, so that in use the coils are tilted at approximately 54.74° to the $B_0$ imaging field. This effectively allows mutual decoupling to occur inherently as a result of the coil arrangement, and as such no mutual decoupling scheme is required. It will be appreciated that by achieving orthogonality between coil elements this can provide high isolation/decoupling power.

The above described techniques are not limited to only to cylindrical structures, but can be applied to a range of different coil geometries. Consequently, depending on the applications and importantly the advantages required, there are no bounded constraints with regards to the conformal structure to which the above described techniques can be applied.

It will be appreciated that in the above described example, a receive-only coil array system is described. However, the techniques are not limited to such a system and can, without any limitations, be applied to the design of transmit-only and transceive coil array systems.

It will further be appreciated that the orthogonal coil arrays are invariant to the direction of the applied $B_0$ imaging field and as such can without any limitation be used with any horizontal, vertical bore and open MRI systems.

It will further be appreciated that the orthogonal coil arrays are invariant to the direction of the $B_0$ imaging field, and can therefore enhance MR images of collagen fibres in light of the magic angle phenomenon.

It will further be appreciated since the orthogonal coil arrays are invariant to the direction of the $B_0$ imaging field, the coil array can without any limitations be used for unguided intravenous MRI applications.

It will further be appreciated that the embodiments described utilizes a knee coil array system but the coil arrays are not limited to only to human MR imaging and can, without any limitations, be applied to animal MR imaging and MR spectroscopy applications.

It will further be appreciated that coil array system designed using the above described techniques can without any limitation be used for multi-nucleus MM applications.

It will further be appreciated that the above described coil arrays will complement the applications of partial parallel imaging and accelerated spatially selective excitation.

Throughout the specification, the aim has been to describe the invention without limiting the invention to any particular combination of alternate features or any particular applications it can be implemented. Persons skilled in the art will therefore appreciate that numerous variations and modifications will become apparent. All such variations and modifications which become apparent to persons skilled in the art, should be considered to fall within the spirit and scope that the invention broadly appearing before described.

The claims defining the invention are as follows:

1. A coil arrangement for use in a magnetic resonance imaging system, the imaging system being for generating a magnetic imaging field in an imaging region, the coil arrangement including three coils for at least one of transmitting, receiving, or transceiving an electromagnetic field, each coil being provided on a cylindrical coil geometry and being mutually orthogonal, wherein each coil is aligned with a respective one of three orthogonal planes to thereby reduce mutual coupling between the coils, and wherein the coil arrangement includes a coil support for supporting the coils, the coil support having a cylindrical surface shape corresponding to the coil geometry and wherein the coil arrangement does not include additional coils overlapping with the mutually orthogonal coils.

2. A coil arrangement according to claim 1, wherein the coil geometry is determined depending on the imaging to be performed.

3. A coil arrangement according to claim 1, wherein the coil geometry conforms to a shape of at least a part of a subject to be imaged.

4. A coil arrangement according to claim 1, wherein the coil geometry is rotationally symmetric about a coil geometry axis.

5. A coil arrangement according to claim 1, wherein the coils are elliptical.

6. A coil arrangement according to claim 1, wherein the coils are provided circumferentially spaced around a coil geometry axis.

7. A coil arrangement according to claim 6, wherein the coils are azimuthally spaced by 120°.

8. A coil arrangement according to claim 1, wherein the coils are aligned at an angle to a coil geometry axis.

9. A coil arrangement according to claim 8, wherein the coils are aligned at an angle of approximately 35° to the coil geometry axis.

10. A coil arrangement according to claim 1, wherein each coil being provided at an intersection between the coil geometry and the orthogonal planes.

11. A coil arrangement according to claim 1, wherein the coil arrangement includes a mutual decoupling means for mutually decoupling the coils.

12. A coil arrangement according to claim 1, wherein, in use, the coils are aligned at an angle offset to an imaging field direction.

13. A coil arrangement according to claim 12, wherein, in use, the coils are provided at an angle of approximately 54.7° to an imaging field direction.

14. A coil arrangement according to claim 1, wherein the coil arrangement is for use in imaging by modulating/encoding a transmitted or received electromagnetic field.

15. A coil arrangement for use in a magnetic resonance imaging system, the imaging system being for generating a magnetic imaging field in an imaging region, the coil arrangement including:
   a) a coil support that has a cylindrical surface shape corresponding to a coil geometry; and,
   b) three coils for at least one of transmitting, receiving or transceiving an electromagnetic field, the coils being supported by the coil support and being mutually orthogonal, wherein each coil is aligned with a respective one of three orthogonal planes, to thereby reduce mutual coupling between the coils, and
   wherein the coil arrangement does not include additional coils overlapping with the mutually orthogonal coils.

16. A method of determining a coil arrangement for use in a magnetic resonance imaging system, the imaging system being for generating a magnetic imaging field in an imaging region, the method including:
- a) determining a coil geometry wherein the coil arrangement includes a coil support for supporting coils, the coil support having a cylindrical surface shape corresponding to the coil geometry;
- b) arranging three orthogonal planes so that each of the planes intersects the coil geometry; and
- c) determining a coil arrangement for each of three coils in accordance with an intersection of a respective plane with the coil geometry so that the three coils are mutually orthogonal to thereby reduce mutual coupling between the coils and so that the coil arrangement does not include additional coils overlapping with the mutually orthogonal coils.

17. A method according to claim 16, wherein the method includes determining the coil geometry in accordance with a shape of at least a part of a subject to be imaged.

18. A method according to claim 17, wherein the coil geometry conforms to the shape of at least a part of a subject to be imaged.

19. A method according to claim 16, wherein the coil geometry is rotationally symmetric about a coil geometry axis.

20. A method according to claim 16, wherein the method includes arranging the planes so that coils are elliptical.

21. A method according to claim 16, wherein the method includes arranging the planes so that coils are circumferentially spaced around a coil geometry axis.

22. A method according to claim 21, wherein the method includes arranging the planes so that the coils are azimuthally spaced by 120°.

23. A method according to claim 16, wherein the method includes arranging the planes at an angle to a coil geometry axis.

24. A method according to claim 23, wherein the planes are arranged at an angle of approximately 35.3° to the coil geometry axis.

* * * * *